(12) United States Patent
Bao et al.

(10) Patent No.: US 8,586,336 B2
(45) Date of Patent: Nov. 19, 2013

(54) NUCLEIC ACID MOLECULE ENCODING XYLOSE ISOMERASE AND XYLOSE ISOMERASE ENCODED BY THE NUCLEIC ACID MOLECULE

(75) Inventors: Xiaoming Bao, JiNan (CN); Yu Shen, JiNan (CN); Ruilei Ge, JiNan (CN)

(73) Assignee: Shandong University, Jinan (CN)

( * ) Notice: Subject to any disclaimer, the term of this patent is extended or adjusted under 35 U.S.C. 154(b) by 0 days.

(21) Appl. No.: 13/388,225

(22) PCT Filed: Jun. 20, 2011

(86) PCT No.: PCT/CN2011/001014
§ 371 (c)(1),
(2), (4) Date: Jan. 31, 2012

(87) PCT Pub. No.: WO2012/113120
PCT Pub. Date: Aug. 30, 2012

(65) Prior Publication Data
US 2012/0225452 A1    Sep. 6, 2012

(30) Foreign Application Priority Data

Feb. 22, 2011    (CN) .......................... 2011 1 0042170

(51) Int. Cl.
| | | |
|---|---|---|
| *C12P 7/06* | (2006.01) | |
| *C12P 7/56* | (2006.01) | |
| *C12P 7/54* | (2006.01) | |
| *C12P 7/40* | (2006.01) | |
| *C12P 13/04* | (2006.01) | |
| *C12P 7/18* | (2006.01) | |
| *C12P 7/20* | (2006.01) | |
| *C12P 33/00* | (2006.01) | |
| *C12P 35/00* | (2006.01) | |
| *C12P 19/24* | (2006.01) | |
| *C12N 9/90* | (2006.01) | |
| *C12N 15/00* | (2006.01) | |
| *C12N 1/20* | (2006.01) | |
| *C12N 1/00* | (2006.01) | |

(52) U.S. Cl.
USPC ........... 435/161; 435/139; 435/140; 435/136; 435/106; 435/158; 435/159; 435/52; 435/47; 435/94; 435/233; 435/320.1; 435/252.3; 435/254.11; 435/254.2

(58) Field of Classification Search
None
See application file for complete search history.

(56) References Cited

U.S. PATENT DOCUMENTS

| | | |
|---|---|---|
| 7,622,284 B2 | 11/2009 | Op Den Camp et al. |
| 2008/0014620 A1 | 1/2008 | Op Den Camp et al. |
| 2010/0035306 A1 | 2/2010 | Op Den Camp et al. |
| 2010/0234581 A1 | 9/2010 | Concilio et al. |

FOREIGN PATENT DOCUMENTS

| | | |
|---|---|---|
| CN | 1703514 A | 11/2005 |
| CN | 1712528 A | 12/2005 |
| CN | 1966678 A | 5/2007 |
| CN | 101283096 A | 10/2008 |
| CN | 101323858 A | 12/2008 |
| WO | WO 2004/099381 A2 | 11/2004 |
| WO | WO 2006/009434 A1 | 1/2006 |
| WO | WO 2010/074577 A1 | 7/2010 |

OTHER PUBLICATIONS

Oct. 27, 2011 International Search Report issued in Chinese Patent Application No. PCT/CN2011/001014 (with translation).
Oct. 27, 2011 Written Opinion of the International Searching Authority issued in International Patent Application No. PCT/CN2011/001014 (with translation).
Xiaoming et al., "Overexpression of Thermophilic Bacteria Xylose Isomerase Gene (xyla) in *Saccharomyces cerevisiae*," *Acta Microbiologica Sinica*, vol. 39, No. 1, pp. 49-54, 1999.
Zhu et al., "Research Progress on Bioengineering of Glucose Isomerase," *Progress in Biochemistry and Biophysics*, vol. 27, Issue 2, pp. 127-131, 2000.
Madhavan et al., "Xylose isomerase from polycentric fungus Orpinomyces: gene sequencing, cloning, and expression in *Saccharomyces cerevisiae* for bioconversion of xylose to ethanol," *Appl Microbiol Biotechnol*, vol. 82, Issue 6, pp. 1067-1078, 2009.
Tasse et al., "Uncultured organism clone 23 genomic sequence" Database Genbank [Online], Registration No. GU942940, 2010.
"Xylose isomerase [*Prevotella buccae* ATCC 33574]" Database Genbank [Online], Registration No. ZP_07883886, 2010.
Ward et al., "Xylose isomerase [*Prevotella buccae* D17]" Database Genbank [Online], Registration No. ZP_06420872, 2010.
"Xylose isomerase [*Prevotella bergensis* DMS 17361]" Database Genbank [Online], Registration No. ZP_06006100, 2010.
Harhangi et al., "xylose isomerase [*Piromyces* sp. E2]" Database Genbank [Online], Registration No. CAB76571, 2005.
Nigam, "Development of xylose-fermenting yeast *Pichia stipitis* for ethanol production through adaptation on hardwood hemicellulous acid prehydrolysate," *Journal of Applied Microbiology*, vol. 90, pp. 208-215, 2001.
Traff et al., "Deletion of the *GRE3* Aldose Reductase Gene and Its Influence on Xylose Metabolism in Recominant Strains of *Saccharomyces cerevisiae* Expressing the xylA and XKS1 Genes," *Journal of Applied and Environmental Microbiology*, vol. 67, No. 12, pp. 5668-5674, 2001.

(Continued)

*Primary Examiner* — David J Steadman
(74) *Attorney, Agent, or Firm* — Oliff & Berridge, PLC (57) ABSTRACT

A novel xylose isomerase nucleotide sequence obtained from a bovine rumen fluid metagenomic library and also provides the amino acid sequence encoded by the nucleotide sequence, and a vector and a transformant containing the nucleotide sequence. When the xylose isomerase is expressed, a host cell is endowed with the capability of converting xylose into xylulose, and the xylulose is further metabolized by the host cell. Therefore, the host cell can take the xylose as a carbon source for growth. The xylose isomerase from a new source is expressed with high activity in *Saccharomyces cerevisiae* and is a mesophilic enzyme with optimal temperature of 60° C.

9 Claims, 3 Drawing Sheets

(56) References Cited

OTHER PUBLICATIONS

Walfridsson et al., "Xylose-Metabolizing *Saccharomyces cerevisiae* Strains Overexpressing the *TKL1* and *TAL1* Genes Encoding the Pentose Phosphate Pathway Enzymes Transketolase and Transaldolase," *Journal of Applied and Environmental Microbiology*, vol. 61, No. 12, pp. 4184-4190, 1995.

Bhosale et al., "Molecular and Industrial Aspects of Glucose Isomerase," *Microbiological Reviews*, vol. 60, No. 2, pp. 280-300, 1996.

Karimaki et al., "Engineering the substrate specificity of xylose isomerase," *Protein Engineering, Design & Selection*, vol. 17, No. 12, pp. 861-869, 2004.

Lonn et at., "Cold adaptation of xylose isomerase from *Thermus thermophilus* through random PCR mutagenesis," *Eur. J. Biochem.*, vol. 269, pp. 157-163, 2002.

Kuyper et al., "High-level functional expression of a fungal xylose isomerase: the key to efficient ethanolic fermentation of xylose by *Saccharomyces cerevisiae?" FEMS Yeast Research*, vol. 4, pp. 69-78, 2003.

Sedlak et al., "Production of Thanol from Cellulosic Biomass Hydrolysates Using Genetically Engineered *Saccharomyces* Yeast Capable of Cofermenting Glucose and Xylose," *Biochemistry and Bootechnology*, vol. 113-116, pp. 403-416, 2004.

Kuyper et al., "Minimal metabolic engineering of *Saccharomyces cerevisiae* for efficient anaerobic xylose fermentation: a proof of principal," *FEMS Yeast Research*, vol. 4, pp. 655-664, 2004.

Tian et al., "Development of Ethanol Production from Lignocellulosic Hydrolysates," *China Academic Journal Electronic Publishing House*, vol. 35, No. 2, pp. 355-358, 2007.

Fig.1
M:1kb DNA Ladder
1:RuXI

Fig.2
M:1kb DNA Ladder
BamHI and SbfI Double-digested Plasmid pJFE-RuXI

NUCLEIC ACID MOLECULE ENCODING XYLOSE ISOMERASE AND XYLOSE ISOMERASE ENCODED BY THE NUCLEIC ACID MOLECULE

BACKGROUND

1. Field of Invention

The invention relates to a novel nucleic acid molecule encoding xylose isomerase and the xylose isomerase encoded by the nucleic acid molecule. The invention relates to the research on enzymological properties of the xylose isomerase. The invention relates to the application of the xylose isomerase in the technical field of enzyme engineering. The invention also relates to a yeast strain containing the introduced nucleic acid sequence encoding the xylose isomerase.

2. Description of Related Art

Due to rising oil prices and global warming caused by greenhouse effect, people put more and more concern on the development and utilization of renewable energy sources. As an important renewable energy, biomass has a broad development space in the production of fuel ethanol as a raw material. For a long time, ethanol is produced by starch and sugars fermentation. Higher costs of the raw materials have greatly limited the development of the biomass fuel ethanol industry. Biomass produced by photosynthesis is up to 150 to 200 billion tons per year globally. Inside, above 80% of biomass are lignocellulosic substances, which are very cheap and easy to obtain. Therefore the production of the fuel ethanol by taking lignocelluloses as raw materials has an important practical significance. The lignocellulose mainly composes by cellulose, hemicelluloses, and lignin. It can be converted to pentose (xylose and arabinose) and hexose (glucose, galactose and mannose) by acidolysis or/and enzymolysis. The xylose is the second abandant monosaccharide, just follow the glucose, in the hydrolysate of lignocelluloses. The percentage of xylose could be up to 30%. Analysis shows that the ethanol yield could increases 25% if the xylose in lignocellulosic materials could be fully convered to ethanol (Nigam et al., J Appl Microbiol, 2001, 90 (2): 208-215). However, the *Saccharomyce cerevisise*, a good ethanol producer, cannot use the xylose as a carbon source. Therefore, constructing the *S. cerevisise* engineering strains that could efficiently utilize xylose to produce ethanol is one of the key issues in the sufficient utilization of lignocellulosic resources.

The natural xylose-utilizing yeasts convert xylose to xylulose, which *S. cerevisise* could metabolize, by two reactions. The xylose is firstly reduced to xylitol under the catalysis of the XR (xylose reductase), and then oxidized to xylulose by the XDH (xylitoldehydrogenase) (Träff et al., Appl Environ Microbiol, 2001, 67: 5668-5674). In most bacteria, such as *Escherichia coli* and *Bacillus* sp., the xylose is directly converted to the xylulose through xylose isomerase (XI) (Träff et al., Appl Environ Microbiol, 2001, 67: 5668-5674). Then, the xylulose is converted to xylulose 5-phosphate catalyzed by xylulose kinase (XK), and enters a pentose phosphate pathway (PPP). *S. cerevisise* has high ethanol productivity, and excellent characteristics such as high tolerance to inhibitors, unfavorable fermentation conditions, and high-concentration ethanol. Furthermore, it is a non-pathogenicity microorganism. However, due to the lack of XR and XDH, the *S. cerevisis* cannot metabolize xylose. To enable the *S. cerevisiae* obtain the ability to ferment the xylose, genes encoding NAD (P) H-depending XR and NAD$^+$-depending XDH were cloned from *Pichia stipitis* and introduced into the *S. cerevisiae* to obtain the recombinant strain, which can be used for producing ethanol by fermenting the xylose (Walfridsson et al., Appl Environ Microbiol, 1995, 61: 4184-4190; Sedlak et al., Appl Biochem Biotechnol, 2004, 113-116: 403-416). But the affinity of XR to NADPH is much higher than that of XR to NADH, which results in cofactor imbalance in the process of oxidizing the xylitol into the xylulose under the catalysis of XDH. As a result, the by-product xylitol and glycerol accumulated and the yield of ethanol decreased. As the xylose isomerase does not need the cofactor, the xylose isomerase attracts the attention of researchers (Kuyper et al., FEMS Yeast Research, 2004, 4: 655-664).

Xylose isomerase, XI (EC5.3.1.5) can catalyze D-xylose into D-xylulose in vivo, and convert D-glucose into D-fructose in vitro, so that the xylose isomerase is also known as glucose isomerase. As the structure of the enzyme is very stable, the xylose isomerase is one of the good models for studying the relationships between protein structure and functions (Karimaki et al., Protein Eng Des Sel, 12004, 17 (12): 861-869). Moreover, the extremely important industrial application value makes the xylose isomerase is seen as important industrial enzyme as protease and amylase (Tian Shen et al., Microbiology Bulletin, 2007, 34 (2): 355-358; Bhosale et al., Microbiol Rev, 1996, 60 (2): 280-300). The scientists keep high concern and carried out extensive research on xylose isomerase. Since 1970s, the applications of the xylose isomerase have focused on the production of high fructose syrup and fuel ethanol. In recent years, scientists have found that under certain conditions, the xylose isomerase can be used for producing many important rare sugars, which are the production materials in the pharmaceutical industry, such as ribose, mannose, arabinose and lyxose (Karimaki et al., Protein Eng Des Se, 12004, 17 (12): 861-869). These findings bring new vitality in the research on the xylose isomerase.

It was reported that although a variety of bacterial sources xylose isomerase genes have been cloned and introduced into the *S. cerevisiae*, the mesophilic prokaryotic XIs cloned from common bacteria cannot functionally express in *S. cerevisiae*. In the about 450 currently published amino acid sequences of the xylose isomerase, two thermophilic bacteria sources XI expressed ~1 U/mg specific activity products in the *S. cerevisiae*, which activity data were determined at 85 DEG C. However, only a very small part of the activity is retained at suitable temperature for *S. cerevisiae* growth (30 DEG C). Some other sources of xylose isomerase genes can express activity in the *S. cerevisiae* were found, including fungi sources, which were *Piromyces* sp-E2, *Orpinomyces* sp-Ukk1 and *Cyllamyces aberensis*; and bacteria sources, which were *Clostridium phytofermentans, Clostridium difficile, Bacteroides Fusobacterium-mortiferum*, and *Ciona intestinalis*. Wherein, only the xylose isomerase genes cloned from the *Piromyces* sp-E2 and *Clostridium phytofermentans*, especially the former, expressed elevated activity in *S. cerevisiae*.

SUMMARY

Aiming at the prior art, the invention provides a mesophilic xylose isomerase from a new source, a gene for encoding the enzyme and a host cell for expressing the enzyme. The invention is realized through the following technical scheme:

A nucleic acid molecule for encoding xylose isomerase, with a sequence being one of the following nucleotide sequences:
(1) The nucleotide sequence shown in SEQ ID NO. 1;
(2) A homologous sequence with at least 40% of sequence identity formed by adding, substituting, deleting or inserting one or more nucleotides in the nucleotide sequence shown in SEQ ID NO. 1;
(3) The nucleotide sequence formed by hybridization with the nucleotide sequence in (1) or (2) under strict conditions;
(4) The nucleotide sequence different from the nucleotide sequence in (3) due to degeneracy of genetic codon.

A sequence of the xylose isomerase is one of the following amino acid sequences:

(1) The amino acid sequence shown in SEQ ID NO. 2;
(2) A homologous sequence with at least 40% of sequence identity formed by adding, substituting, deleting or inserting one or more amino acids in the amino acid sequence shown in SEQ ID NO. 2.

Amino acids encoded by nucleotides for encoding the xylose isomerase do not include the amino acid sequences selected from the following groups:

(1) The sequence of *Piromyces* sp-E2 xylose isomerase disclosed in WO 03/062340;
(2) The sequence of *Bacteroides thetaiotaomicron* xylose isomerase disclosed in WO 04/099381 and WO 06/009434;
(3) The sequence of *Cyllamyces aberensis* xylose isomerase disclosed in WO 04/099381;
(4) The sequence of *Orpinomyces* sp-Ukk1 xylose isomerase disclosed in Madhavan et al. (2009, supra);
(5) The sequence of *Clostridium difficile, Fusobacterium-mortiferum* and *Ciona intestinalis* xylose isomerase disclosed in WO 2010/074577.

The amino acid sequences encoded by nucleotides for encoding xylose isomerase do not include the amino acid sequences selected from the following groups: the amino acid sequences with sequence identity higher than that of the amino acid sequences selected from the following groups by 99, 98, 97, 96, 95, 94, 93, 92, 91, 90, 89, 88, 87, 86, 85, 84, 83, 82, 81, 80, 79, 78, 77, 76, 75, 74, 73, 72, 71 or 70%.

(1) The sequence of *Piromyces* sp-E2 xylose isomerase disclosed in WO 03/062340;
(2) The sequence of *Bacteroides thetaiotaomicron* xylose isomerase disclosed in WO 04/099381 and WO 06/009434;
(3) The sequence of *Cyllamyces aberensis* xylose isomerase disclosed in WO 04/099381;
(4) The sequence of *Orpinomyces* sp-Ukk1 xylose isomerase disclosed in Madhavan et al. (2008, supra);
(5) The sequence of *Clostridium difficile, Fusobacterium-mortiferum*, and *Ciona intestinalis* xylose isomerase disclosed in WO 2010/074577.

The applications of the xylose isomerase in the fields such as chemical industry, food, and medical treatment.

The xylose isomerase has extremely important industrial application value, and the applications of the xylose isomerase mainly focus on the production of high fructose syrup and fuel ethanol. Under certain conditions, the xylose isomerase can be used for producing many important rare sugars, which are the production materials in the pharmaceutical industry, such as ribose, mannose, arabinose and lyxose. As the structure of the enzyme is very stable, the xylose isomerase is one of the good models for studying the relationship between protein structure and functions.

A recombinant vector contains the nucleic acid sequence, which is the complete encoding reading frame of the xylose isomerase.

A host cell, originated from the bacterium, yeast or filamentous fungus, and preferably is the yeast with the capacity of anaerobic ethanol fermentation; and the host cell contains the recombinant vector; and the xylose isomerase encoding nucleotide sequence is operatively connected with the promoter, which could cause the expression of the xylose isomerase in the host cell, so as to endow the host cell with the ability to isomerize xylose into xylulose.

The host cell preferably contains active glycolysis pathway, a pentose phosphate pathway and xylulose kinase activity, so that the xylulose obtained from the isomerization of the xylose can be metabolized into pyruvic acid in the host cell.

The host cell preferably contains enzyme for converting the pyruvic acid into desired catabolites such as ethanol, ethylene or lactic acid.

The host cell preferably is the yeast with the capacity of anaerobic ethanol fermentation.

The host cell preferably has tolerance to ethanol and organic acids such as acetic acid, lactic acid or formic acid, as well as sugar derivative, such as furfural and HMF.

The host cell has these characteristics or enzyme activities naturally or obtains these characteristics or enzyme activities through genetic modification.

The host cell contains a genetic modification, which reduces non-specific aldose reductase activity.

The host cell has the capacity of converting L-arabinose into D-xylulose 5-phosphate.

The host cell contains one or more genetic modifications, which lead to the characteristics listed below:

(1) Increase in xylose absorption of the host cell;
(2) Enhancement of the activity of xylulokinase;
(3) Increase in flow rate of the pentose phosphate pathway;
(4) Reduction of sensitivity to catabolite repression;
(5) Enhancement of tolerance to ethanol, osmotic stress or organic acid;
(6) Decrease in by-product generation;
(7) Blocking of respiratory electron-transport chain.

The by-products are defined as the carbon containing compounds produced rather than the desired fermentation products, including xylitol, glycerol, and acetic acid.

Genetic modifications consist of over-expression of endogenous genes, expression of heterologous genes or combinations thereof, and genes are selected from the following genes: hexose or pentose transporter genes, xylulokinase genes, genes encoding the enzymes in pentose phosphate pathway, genes encoding the glycolytic enzymes or/and genes related to ethanol fermentation.

The host cell expresses one or more enzymes, and is endowed with the capability of producing a series of metabolites such as lactic acid, acetic acid, succinic acid, amino acid, 1,3-propylene glycol, ethylene, glycerol, beta-lactam antibiotics or/and cephalosporins by the enzymes.

A method for producing fermentation products by the recombinant cell: the host cell is fermented in a culture medium containing a xylose raw material or/and a glucose raw material, and then the fermentation products are separated and purified, wherein the fermentation products are lactic acid, acetic acid, succinic acid, amino acid, 1,3-propylene glycol, ethylene, glycerol, beta-lactam antibiotics or/and cephalosporins.

The capability of the transformed host cell of isomerizing xylose to xylulose is to directly isomerize xylose into xylulose, which is different from the transformation of xylose into xylulose through xylitol by two transitional steps, under the catalysis of xylose reductase and xylitol dehydrogenase respectively.

Figure 3:
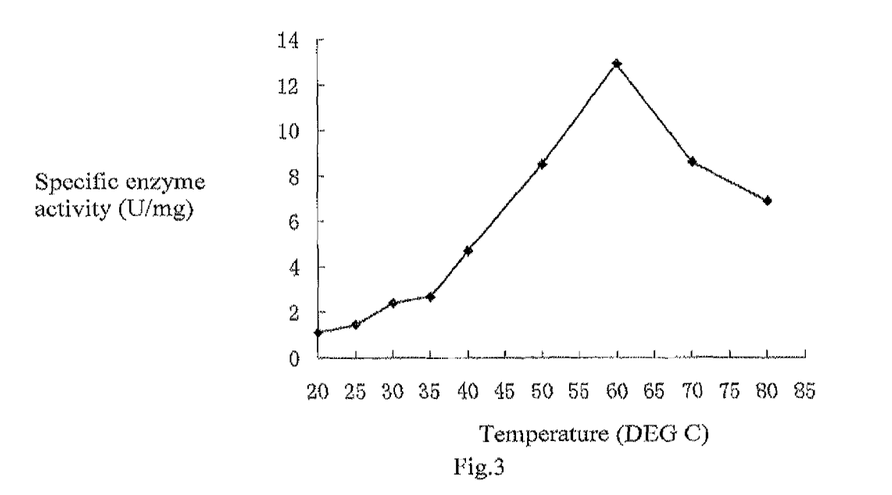
FIG. 3: Determination of the optimum temperature of novel xylose isomerase expressed by *S. cerevisiae* transformant.

The nucleotide sequence for encoding xylose isomerase is expressed in the host cell in the activitive form, therefore, the nucleotide sequence is expressed in the host cell to generate xylose isomerase with specific activity. The specific activity of the xylose isomerase expressed in the host cell is defined as unitage (U) of xylose isomerase activity per mg of protein in cell-free lysate of the host cell such as cell-free lysate of yeast. The determination of xylose isomerase activity, protein content and preparation of cell-free lysate are described in the following embodiment 2. The novel xylose isomerase expressed high-activity in *S. cerevisiae*. The xylose isomerase activity is determined by adopting an XI-SDH one-step method at 30 DEG C (Kuyper et al., FEMS Yeast Research, 2003, 4:69-78), and the enzyme activity is 1.3 U/mg, which is higher than the activity of xylose isomerase from *Piromyces* sp-E2 source being 1.1 U/mg (Kuyper et al., FEMS Yeast Research, 2003, 4:69-78). The xylose isomerase from the new source is a mesophilic xylose isomerase, with the optimum temperature of 60 DEG C (FIG. 3).

DETAILED DESCRIPTION

The invention is further illustrated in combination with embodiments as follows.

Embodiment 1 A DNA Sequence of Xylose Isomerase from a Bovine Rumen Fluid Metagenomic Library was Cloned The clone of partial DNA sequence encoding xylose isomerase between conserved domains of xylose isomerase:

By taking a bovine rumen fluid metagenomic library as a template annealed with the primers XIcF and XIcR (Table 1), the product of PCR, which is ~400 bp, was purified and connected into a T vector. 22 recombinant vectors with different PCR fragments were selected randomly and sequenced. Sequencing results show that the sequences of the 22 cloned DNA inserting fragments all belong to specific sequences of xylose isomerase, wherein 21 DNA fragments are part of xylose isomerase gene of *E. coli*, and only one cloned DNA inserting fragment belongs to the xylose isomerase gene conserved sequence from a new source. The fragments were named as 2PXI-3 and 374 bp.

TABLE 1

Primers used in this work

| SEQ ID NO: | Primer | Sequence(5'→3') |
|---|---|---|
| 3 | XIcF (18 bp) | TGGGG(A/T/C/G)GG(A/T/C/G)CG(A/T/C/G)GA(G/A)GG(A/T/C/G) |
| 4 | XIcR (23 bp) | GG(A/G)AA(T/C)TG(A/G)TC(A/T/C/G)GT(A/G)TCCCA(A/T/C/G)CC |
| 5 | pBK-F | GCCGCTCTAGAAGTACTCTCGAGA |
| 6 | pBK-R | ATGACCTTGATTACGCCAAGCTCG |
| 7 | pBK-R1 | ATTAGGCACCCCAGGCTTTACACT |
| 8 | 2PX I-F | CAGAAGCGTGAGAAGGAGCACATG |
| 9 | 2PX I-R | GTGACCAGCCAATGTAGCGTGGTT |
| 10 | 2PX I-F2 | GATGCTGGGTATGGCTCGTGACTA |
| 11 | 2PX I-R2 | CAGCATACCAGCGTCAACAGCACA |
| 12 | BamHI-GXI-F | GCTCGGATCCATGGCAAAAGAATATTTTCCG |
| 13 | SbfI-GXI-R | CATACCTGCAGGTTATTTGCAGTGGAGGGCGA |

Cloning the 5' and 3' DNA Sequences of Xylose Isomerase:

According to the DNA sequence information of vector pBK-CMV and 2PXI-3, seven specific primers were designed: pBK-F, pBK-R, pBK-R1, 2PXI-F, 2PXI-R, 2PXI-F2, and 2PXI-R2 (Table 1). By taking the bovine rumen fluid metagenomic library as a template, the upstream and downstream of the DNA fragment 2PXI-3 were amplified by PCR, respectively. Using primers pBK-R1 and 2PXI-F, the DNA fragment FT1 containing the 3' part of RuXI was obtained; and using primers pBK-F and 2PXI-R, the DNA fragment PR containing the 5' part of RuXI was obtained.

The Clone of Full-Length DNA Sequence of Xylose Isomerase:

The 5' sequence information (sequence of PR) and 3' sequence information (sequence of FT1) were spliced, and the Open Reading Frames (ORF) of xylA gene can be found in the spliced sequence. Using BamHI-GXI-F and SbfI-GXI-R (Table 1) as specific primers and bovine rumen fluid metagenomic library as the template, a 1320 bp xylA gene was amplified by PCR, and named as RuXI, the sequence was shown in SEQ ID NO. 1.

Embodiment 2 Express the RuXI in *S. cerevisiae*

Construction of Yeast Expression Vector:

The pfu DNA polymerase was used in PCR reaction. The 5' and 3' primers for cloning RuXI were designed base on the sequences of xylose isomerase gene, and SbfI and BamHI restriction sites were contained in the primers, respectively.

The PCR product was cloned into pJFE3 vector to obtain recombinant plasmid pJFE3-RuXI.

Construction of Recombinant *S. cerevisiae* Containing the Xylose Isomerase Gene:

The plasmid pJFE3-RuXI with the xylose isomerase gene was transformed into the *S. cerevisiae*. In the host *S. cerevisiae*, the genes in PPP, which are RPE1, RKI1, TAL1, and TKL1, together with XKS1 were over-expressed, and the gene GRE3 encoding aldose reductase was knockouted; and adaptive evolution was performed in the medium using xylose as the sole carbon source, and the respiratory pathway was blocked. The transformants were screened on a SC-URA plate, and cells which were not transformed cannot grow on the plate.

Recover the Plasmids from Recombinant *S. cerevisiae* Transformants and Verify that the Xylose Isomerase Expressed in the Recombinant Cell has the Right Amino Acid Sequence Shown in SEQ ID NO. 2:

Plasmids in the recombinant *S. cerevisiae* were recovered by Yeast Plasmid Kit. The fact that the xylose isomerase expressed in the recombinant cell is the amino acid sequence shown in SEQ ID NO. 2 can be verified from two aspects: (1) by taking the recovered plasmids as the template, RuXI can be amplified by the specific primers BamHI-GXI-F and SbfI-GXI-R (Table 1) in PCR; and (2) the recovered plasmids were transformed into *E. coli* DH5α and then extracted from the *E. coli* cultivation, then the extracted plasmids were double-digested by BamHI and SbfI. Meanwhile, the extracted plasmids were sequenced to determine if the sequence is as same as the cloned gene RuXI.

Figure 1:
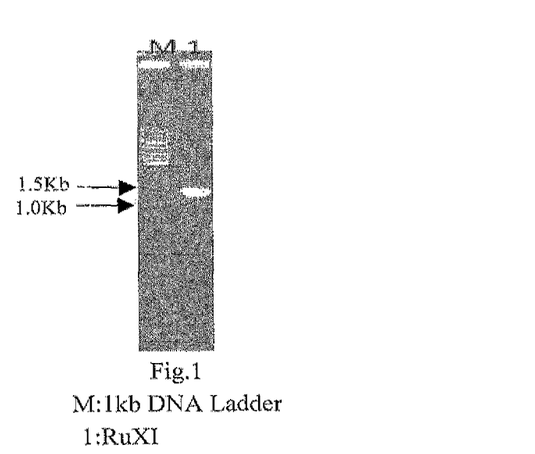
FIG. 1: Verifying that the recombinant cell contains a xylose isomerase gene RuXI. By taking the recovered plasmid from the recombinant yeast as a template, RuXI was amplified by PCR using specific primers BamHI-GXI-F and SbfI-GXI-R (Table 1). M: Marker, 1 kbDNA ladder 1: RuXI.
Figure 2:
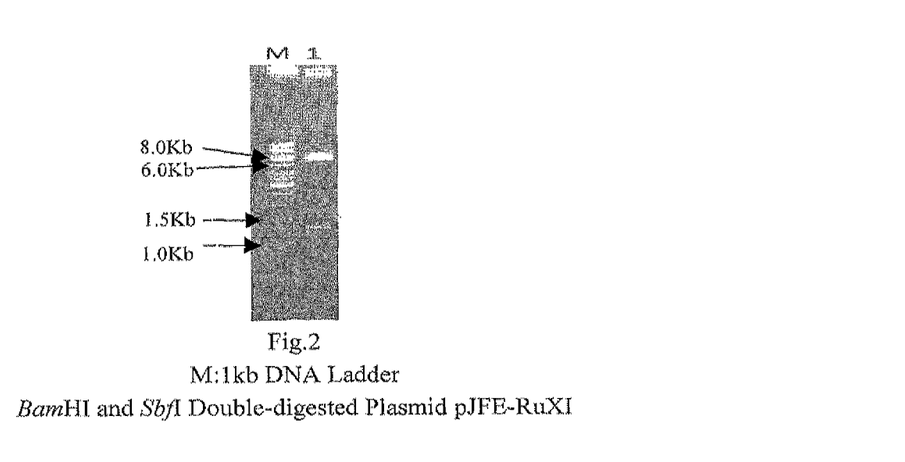
FIG. 2: Verifying that the recombinant cell contains the xylose isomerase gene RuXI. The recovered plasmids were transformed into *E. coli* DH5α, then the plasmids extracted from recombinant *E. coli* DH5α cultivation were double-digested by BamHI and SbfI, the DNA fragments obtained were identified by electrophoresis. M: Marker, 1 kb DNA ladder 1: RuXI (~1.3 kb) and linear vector pJFE3 (~0.6 kb)

Results:

Sequencing result of the plasmids extracted from the recombinant *S. cerevisiae* show that the target gene sequence was consistent with the nucleotide sequence shown in SEQ ID NO. 1, and the length of fragments obtained by PCR (FIG. 1) and enzyme digestion (FIG. 2) also demonstrate that the nucleotide sequence shown in SEQ ID NO. 1 had been transferred into the *S. cerevisiae*, namely, the xylose isomerase expressed in the recombinant cell is the amino acid sequence shown in SEQ ID NO. 2.

Expression:

The transformed yeast cell was cultured in glucose medium for 12 h at 30 DEG C, the initial OD was about 0.2. The cell was recovered and dissolved by using glass beads (0.10-0.11 mm) and lysis buffer (100 mM Tris-HCl contains protease inhibitor), and disrupted by using a mechanical vibration cell disruption apparatus, and the mixture was centrifuged after cell disruption (11,000 g, 4 DEG C, 10 min).

The xylose isomerase activity in clarified supernatant, which is the crude enzyme solution, was determined by XI-SDH one-step method (100 mM, Tris-HCl, pH7.5; 500 mM xylose, 10 mM $MgCl_2$, crude enzyme solution 10 µl, 1 U SDH, 0.15 mM NADH, the amount of oxidized NADH was detected at 340 nm, namely time scanning was conducted at 340 nm) (Kuyper et al., FEMS Yeast Research, 2003, 4:69-78).

As the SDH used in the determination method of xylose isomerase activity requires appropriate reaction temperature, the XI-SDH two-step method was adopted in the determination of the optimal temperature of the xylose isomerase (Lönn et al., European Journal of Biochemistry, 2002, 269 (1): 157-163). The first-step reaction: 100 mM, Tris-HCl pH7.5, 500 mM xylose, 10 mM $MgCl_2$, crude enzyme solution 10 ul. 50% trichloroacetic acid was used to terminate the reaction, and 2M sodium carbonate was used for neutralizing the reaction. The second-step reaction: 100 ul reaction solution in the previous step was taken, 100 mM Tris-HCl pH7.5, 1 U SDH, 0.3 mM NADH, the amount of oxidized NADH was detected at 340 nm, namely time scanning was conducted at 340 nm. Under the conditions of 100 mM Tris-HCl pH7.5, 10 mM $MgCl_2$, the enzyme activity of the xylose isomerase at 20 DEG C, 25 DEG C, 30 DEG C, 35 DEG C, 40 DEG C, 50 DEG C, 60 DEG C, 70 DEG C and 80 DEG C were determined (FIG. 3). The determination of protein content refers to Comassie Blue Method of Bradford (1976).

Conclusions: The xylose isomerase was expressed in *S. cerevisiae* with a high activity. The invention relates to a xylose isomerase which is a mesophilic xylose isomerase, with the optimum temperature of 60 DEG C (FIG. 3). The xylose isomerase activity was determined by adopting the XI-SDH one-step method at 30 DEG C (Kuyper et al., FEMS Yeast Research, 2003, 4:69-78), and the enzyme activity is 1.3 U/mg, which is higher than the activity of xylose isomerase of *Piromyces* sp-E2 being 1.1 U/mg (the data come from determination experiment in a same batch, meanwhile the data are consistent with reports of the document Kuyper et al., FEMS Yeast Research, 2003, 4:69-78).

Embodiment 3 Growth and Fermentation of Transformed Yeast Strain on Xylose

Medium Composition:

The *S. cerevisiae* grows in SC medium containing the following components: 0.67 (w/v) % yeast nitrogen base; and CSM-URA, which is the mixture of purines, pyrimidines, and amino acids except for uracil. For the plate, 1.8% of agar was added in the medium, and pH was adjusted to 6.5 to 7.0.

Growth of Strains:

Host *S. cerevisiae* strain BSPX042 (phenotype: ura3-251, overexpression of XKS1; overexpression of RPE1, RKI1, TAL1, and TKL1, which are genes in PPP; knockout of aldose reductase gene GRE3; and damage of electron transport respiratory chain by deleting gene COX4 after adaptive evolution), was transformed by empty vector pJFE3 and vector pJFE3-RuXI inserted with xylose isomerase gene from a new source, respectively, to obtain recombinant strains BSGX000 and BSGX001 respectively. The two recombinant strains were cultured in SC liquid medium taking 2% glucose and 2% xylose as carbon source, and SC liquid medium taking 2% xylose as a sole carbon source, respectively. The growth is monitored by determining the increasing of optical density in a spectrophotometer at 600 nm.

Figure 4:
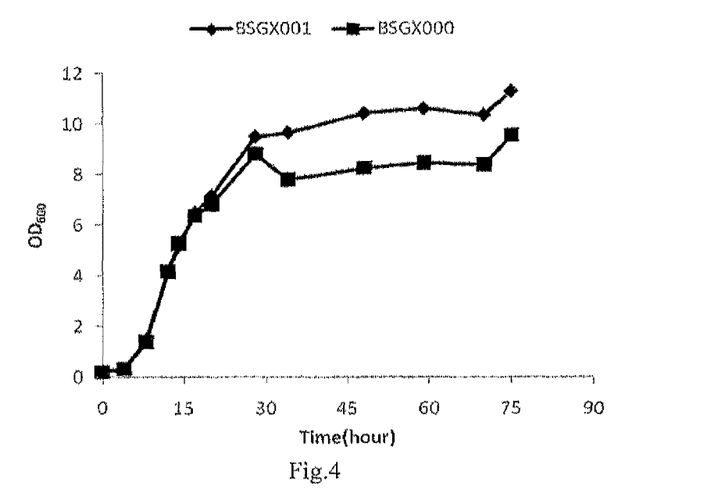
FIG. 4: Growth curve of *S. cerevisiae* transformant in culture medium containing 20 g/L glucose and 20 g/L xylose as carbon sources.
Figure 5:
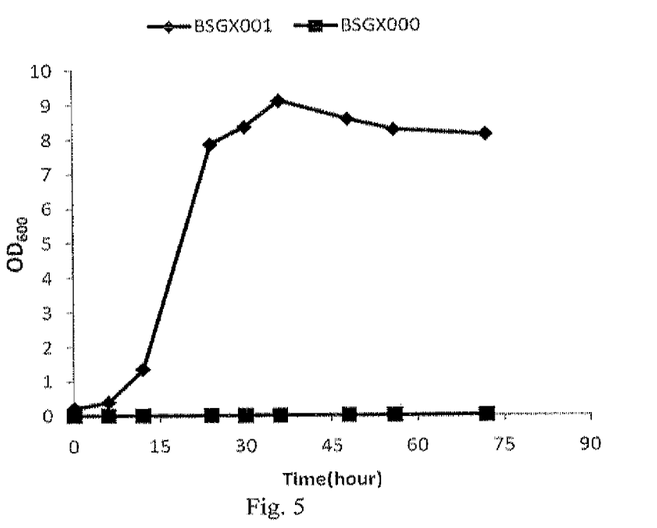
FIG. 5: Growth curve of *S. cerevisiae* transformant in culture medium containing 20 g/L xylose as a sole carbon source.

Results:

Results of growth experiment are shown in FIG. 4 and FIG. 5. In the SC liquid medium taking 2% glucose and 2% xylose as the carbon source, the recombinant strains BSGX000 and BSGX001 had similar growth trends in glucose consumption stage, with $\mu_{max}$ (maximum specific growth rate) being 0.31 respectively. After glucose depletion, BSGX001 grew better than BSGX000 (FIG. 4). In the SC liquid medium taking 2% xylose as the sole carbon source, the recombinant strain BSGX000 which does not contain the xylose isomerase gene did not grow; and the recombinant strain BSGX001 containing the xylose isomerase gene RuXI grew better, with $\mu_{max}$ being 0.16 (FIG. 5).

Embodiment 4 Oxygen-Limited Fermentation of Transformed Yeast Strain Taking Xylose as the Sole Carbon Source Medium Composition and Fermentation:

SC liquid medium: 0.67 (w/v) % yeast nitrogen base; and CSM-URA; and 2% xylose.

The oxygen-limited fermentation of the recombinant strain BSGX001 was performed in the 100 mL oxygen-limited bottle containing SC liquid medium taking 2% xylose as the sole carbon source. The fermentation was continued for 72 h, and samples were taken and the metabolites were analyzed by HPLC.

Figure 6:
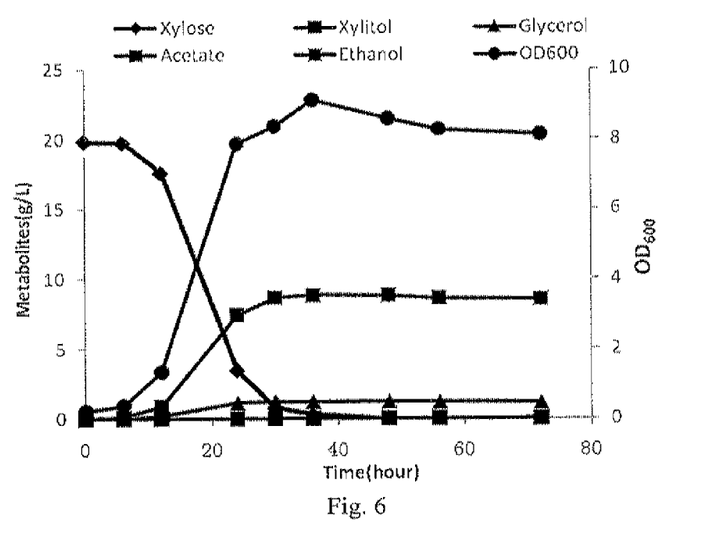
FIG. 6: The metabolites concentration of *S. cerevisiae* transformant in oxygen-limited fermentation of 20 g/L xylose.

Results:

The recombinant strain BSGX001 containing the xylose isomerase was subjected to oxygen-limited fermentation in the SC liquid medium taking 2% xylose as the sole carbon source, the ethanol yield reached 0.24 gram per gram biomass per hour, the conversion rate of sugar alcohol was up to 44%, and no detectable by-product xylitol was generated (FIG. 6).

What is claimed is:

1. An isolated polypeptide having xylose isomerase activity comprising:
   (1) the amino acid sequence set forth in SEQ ID NO: 2; or
   (2) an amino acid sequence having at least 90% amino acid sequence identity with the amino acid sequence set forth in SEQ ID NO: 2.

2. A recombinant vector comprising an isolated nucleic acid molecule encoding the isolated polypeptide of claim 1.

3. A recombinant bacterium, yeast or filamentous fungus cell comprising the recombinant vector of claim 2.

4. The recombinant cell of claim 3, wherein the recombinant cell expresses one or more enzymes, and is capable of producing lactic acid, acetic acid, succinic acid, an amino acid, 1,3-propylene glycol, ethylene, glycerol, β-lactam antibiotics, and/or cephalosporins.

5. A method for producing fermentation products comprising culturing the recombinant cell of claim 4 in a culture medium containing xylose and/or glucose to produce fermentation products, and then the fermentation products are separated and purified from the culture medium, wherein the fermentation products are lactic acid, acetic acid, succinic acid, amino acid, 1,3-propylene glycol, ethylene, glycerol, β-lactam antibiotics and/or cephalosporins.

6. A method of converting D-xylose to D-xylulose or converting D-glucose to D-fructose comprising contacting D-xylose or D-glucose with the isolated polypeptide according to claim 1 to produce D-xylulose or D-fructose, respectively.

7. The recombinant vector of claim 2, wherein the amino acid sequence of the encoded isolated polypeptide has at least 95% amino acid sequence identity with the amino acid sequence set forth in SEQ ID NO: 2.

8. The isolated polypeptide of claim 1, wherein the amino acid sequence of the isolated polypeptide has at least 95% amino acid sequence identity with the amino acid sequence set forth in SEQ ID NO: 2.

9. A method for producing ethanol, comprising:
culturing under anaerobic fermentation conditions a recombinant yeast cell of claim 3 in a culture medium containing xylose to produce ethanol.

* * * * *

SEQUENCE LISTING

<160> NUMBER OF SEQ ID NOS: 13

<210> SEQ ID NO 1
<211> LENGTH: 1320
<212> TYPE: DNA
<213> ORGANISM: Bovine

<400> SEQUENCE: 1

```
atggcaaaag aatattttcc gtttactggt aaaattcctt tcgagggaaa ggatagtaaa      60
aatgtaatgg ctttccatta ttacgagccc gagaaagtcg tgatgggaaa gaagatgaag     120
gactggctga agttcgcaat ggcctggtgg cacacactgg gaggcgcttc tgcagaccag     180
ttcggtggtc aaactcgcag ctatgagtgg acaaggctaa atgcccgt acagcgtgca       240
aaggataaga tggacgctgg tttcgagatc atggataagc tgggtatcga gtacttctgc     300
ttccacgatg tagacctcgt tgaggaggct cccaccatcg ctgagtacga ggagcgcatg     360
aaggccatca ccgactacgc tcaggagaag atgaagcagt tccccaatat caagctgctc     420
tggggtaccg caaacgtatt cggcaacaag cgttatgcca atggcgcttc taccaacccc     480
gatttcgatg tggttgctcg tgcgattgtt cagatcaaga actctatcga cgctaccatc     540
aagcttggtg gtaccaacta tgtgttctgg ggtggtcgtg agggctacat gagcctgttg     600
aacaccgacc agaagcgtga aggagcac atggctacga tgctgggtat ggctcgtgac      660
tatgctcgcg ctaagggatt caagggtacg ttcctgattg agccgaagcc gatggagcct     720
tcaaagcacc agtatgatgt ggacacagag accgtgattg gcttcctgaa ggcacatggt     780
ctggataagg acttcaaggt gaacatcgag gtgaaccacg ctacattggc tggtcacacc     840
ttcgagcacg aactggcttg tgctgttgac gctggtatgc tgggttctat cgacgctaac     900
cgcggtgatg cccagaacgg ctgggatacc gaccagttcc ccatcgacaa ctttgagctg     960
acacaggcta tgctggagat catccgcaac ggtggtctgg gcaatggcgg taccaatttc    1020
gacgccaaga tccgtcgtaa ttctaccgac ctcgaggatc tcttcatcgc tcatatcagc    1080
ggtatggatg ccatggcccg cgccctgatg aatgcagccg atattcttga gaactctgaa    1140
ctgccccgcaa tgaagaaggc tcgctacgca agcttcgaca gcggtatcgg taaggacttc    1200
gaggatggca agctgaccct cgagcaggtt tacgagtatg taagaaggt tgaagagccg     1260
aagcagacct ctggcaagca ggagaagtac gagacaatcg tcgccctcca ctgcaaataa    1320
```

<210> SEQ ID NO 2
<211> LENGTH: 439
<212> TYPE: PRT
<213> ORGANISM: Artificial Sequence
<220> FEATURE:
<223> OTHER INFORMATION: Synthetic Construct-An amino acid sequence of
      xylose isomerase

<400> SEQUENCE: 2

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Cys Pro Val Gln Arg Ala

```
                65                  70                  75                  80
Lys Asp Lys Met Asp Ala Gly Phe Glu Ile Met Asp Lys Leu Gly Ile
                        85                  90                  95

Glu Tyr Phe Cys Phe His Asp Val Asp Leu Val Glu Glu Ala Pro Thr
                    100                 105                 110

Ile Ala Glu Tyr Glu Arg Met Lys Ala Ile Thr Asp Tyr Ala Gln
                115                 120                 125

Glu Lys Met Lys Gln Phe Pro Asn Ile Lys Leu Leu Trp Gly Thr Ala
            130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ser Ile
                    165                 170                 175

Asp Ala Thr Ile Lys Leu Gly Gly Thr Asn Tyr Val Phe Trp Gly Gly
                180                 185                 190

Arg Glu Gly Tyr Met Ser Leu Leu Asn Thr Asp Gln Lys Arg Glu Lys
            195                 200                 205

Glu His Met Ala Thr Met Leu Gly Met Ala Arg Asp Tyr Ala Arg Ala
        210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                    245                 250                 255

Lys Ala His Gly Leu Asp Lys Asp Phe Lys Val Asn Ile Glu Val Asn
                260                 265                 270

His Ala Thr Leu Ala Gly His Thr Phe Glu His Glu Leu Ala Cys Ala
            275                 280                 285

Val Asp Ala Gly Met Leu Gly Ser Ile Asp Ala Asn Arg Gly Asp Ala
        290                 295                 300

Gln Asn Gly Trp Asp Thr Asp Gln Phe Pro Ile Asp Asn Phe Glu Leu
305                 310                 315                 320

Thr Gln Ala Met Leu Glu Ile Ile Arg Asn Gly Gly Leu Gly Asn Gly
                    325                 330                 335

Gly Thr Asn Phe Asp Ala Lys Ile Arg Arg Asn Ser Thr Asp Leu Glu
                340                 345                 350

Asp Leu Phe Ile Ala His Ile Ser Gly Met Asp Ala Met Ala Arg Ala
            355                 360                 365

Leu Met Asn Ala Ala Asp Ile Leu Glu Asn Ser Glu Leu Pro Ala Met
        370                 375                 380

Lys Lys Ala Arg Tyr Ala Ser Phe Asp Ser Gly Ile Gly Lys Asp Phe
385                 390                 395                 400

Glu Asp Gly Lys Leu Thr Phe Glu Gln Val Tyr Glu Tyr Gly Lys Lys
                    405                 410                 415

Val Glu Glu Pro Lys Gln Thr Ser Gly Lys Gln Glu Lys Tyr Glu Thr
                420                 425                 430

Ile Val Ala Leu His Cys Lys
            435

<210> SEQ ID NO 3
<211> LENGTH: 18
<212> TYPE: DNA
<213> ORGANISM: Artificial Sequence
<220> FEATURE:
<223> OTHER INFORMATION: Synthetic COnstruct-XIcF Primer
<220> FEATURE:
<221> NAME/KEY: misc_feature
```

```
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 3
tggggnggnc gngarggn                                                   18

<210> SEQ ID NO 4
<211> LENGTH: 23
<212> TYPE: DNA
<213> ORGANISM: Artificial Sequence
<220> FEATURE:
<223> OTHER INFORMATION: Synthetic Construct-XIcR Primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 4
ggraaytgrt cngtrtccca ncc                                             23

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct-pBK-F Primer

<400> SEQUENCE: 5
gccgctctag aagtactctc gaga                                            24

<210> SEQ ID NO 6
<211> LENGTH: 24
<212> TYPE: DNA
<213> ORGANISM: Artificial Sequence
<220> FEATURE:
<223> OTHER INFORMATION: Synthetic Construct-pBK-R Primer

<400> SEQUENCE: 6
atgaccttga ttacgccaag ctcg                                            24

<210> SEQ ID NO 7
<211> LENGTH: 24
<212> TYPE: DNA
<213> ORGANISM: Artificial Sequence
<220> FEATURE:
<223> OTHER INFORMATION: Synthetic Construct-pBK-R1 Primer

<400> SEQUENCE: 7
attaggcacc ccaggcttta cact                                            24

<210> SEQ ID NO 8
<211> LENGTH: 24
<212> TYPE: DNA
<213> ORGANISM: Artificial Sequence
```

-continued

```
<220> FEATURE:
<223> OTHER INFORMATION: Synthetic Construct-2PX I-F Primer

<400> SEQUENCE: 8
cagaagcgtg agaaggagca catg                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic Construct-2PX I-R Primer

<400> SEQUENCE: 9
gtgaccagcc aatgtagcgt ggtt                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic Construct-2PX I-F2 Primer

<400> SEQUENCE: 10
gatgctgggt atggctcgtg acta                                              24

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct-2PX I-R2 Primer

<400> SEQUENCE: 11
cagcatacca gcgtcaacag caca                                              24

<210> SEQ ID NO 12
<211> LENGTH: 31
<212> TYPE: DNA
<213> ORGANISM: Artificial Sequence
<220> FEATURE:
<223> OTHER INFORMATION: Synthetic Construct-BamHI-GXI-F Primer

<400> SEQUENCE: 12
gctcggatcc atggcaaaag aatattttcc g                                      31

<210> SEQ ID NO 13
<211> LENGTH: 32
<212> TYPE: DNA
<213> ORGANISM: Artificial Sequence
<220> FEATURE:
<223> OTHER INFORMATION: Synthetic Construct-SbfI-GXI-R Primer

<400> SEQUENCE: 13
catacctgca ggttatttgc agtggagggc ga                                     32
```